US007325560B2

(12) United States Patent
Arno et al.

(10) Patent No.: US 7,325,560 B2
(45) Date of Patent: *Feb. 5, 2008

(54) IN-SITU GAS BLENDING AND DILUTION SYSTEM FOR DELIVERY OF DILUTE GAS AT A PREDETERMINED CONCENTRATION

(75) Inventors: Jose I. Arno, Brookfield, CT (US); James A. Dietz, Allison Park, PA (US)

(73) Assignee: Advanced Technology Materials, Inc., Danbury, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/453,700

(22) Filed: Jun. 15, 2006

(65) Prior Publication Data

US 2006/0237061 A1    Oct. 26, 2006

Related U.S. Application Data

(63) Continuation of application No. 10/402,759, filed on Mar. 28, 2003, now Pat. No. 7,063,097.

(51) Int. Cl.
*G05D 11/13* (2006.01)

(52) U.S. Cl. .............................. 137/93; 137/3; 137/605

(58) Field of Classification Search .................... 137/3, 137/88, 93, 101.19, 605, 606, 607
See application file for complete search history.

(56) References Cited

U.S. PATENT DOCUMENTS 3,342,199 A    9/1967   McEvoy
4,042,344 A    8/1977   Callcott et al.
4,275,752 A *  6/1981   Collier et al. ................... 137/7
4,564,761 A    1/1986   Buckwald et al.
4,705,669 A * 11/1987   Tsuji et al. .................... 422/93
4,768,291 A    9/1988   Palmer
4,936,877 A    6/1990   Hultquist et al.
5,054,309 A * 10/1991   Mettes et al. ................. 73/1.03
5,118,945 A    6/1992   Winschuh et al.
5,129,412 A *  7/1992   Hendry .......................... 137/1
5,200,023 A    4/1993   Gifford et al.

(Continued)

OTHER PUBLICATIONS

Perry, R.H., et al., Perry's Chemical Engineers' Handbook (7th Edition), 1997, pp. Secs. 6, 8, 16, 18, Publisher: McGraw-Hill, Published in: New York, NY.

*Primary Examiner*—Ramesh Krishnamurthy
(74) *Attorney, Agent, or Firm*—Vincent K. Gustafson; Intellectual Property/Technology Law; David M. Shofi

(57) ABSTRACT

Apparatus and method for delivery of dilute active fluid, e.g., to a downstream active fluid-consuming process unit of a semiconductor manufacturing plant. The delivery system includes an active fluid source, a diluent fluid source, a fluid flow metering device for dispensing of the active fluid at a predetermined flow rate, a mixer arranged to mix active gas from the active fluid source that is dispensed at such predetermined flow rate by the fluid flow metering device, with diluent fluid to form a diluted active fluid mixture, and a monitor arranged to measure concentration of active fluid in the diluted active fluid mixture, and responsively adjust the fluid flow metering device, to control the dispensing rate of the active fluid, and maintain a predetermined concentration of active fluid in the diluted active fluid mixture.

41 Claims, 4 Drawing Sheets

U.S. PATENT DOCUMENTS

| | | |
|---|---|---|
| 5,239,856 A | 8/1993 | Mettes et al. |
| 5,279,146 A | 1/1994 | Asano et al. |
| 5,376,409 A | 12/1994 | Kaloyeros et al. |
| 5,403,089 A * | 4/1995 | Kuo et al. ............ 366/132 |
| 5,436,457 A | 7/1995 | Tomita |
| 5,470,390 A | 11/1995 | Nishikawa et al. |
| 5,508,934 A | 4/1996 | Moslehi et al. |
| 5,518,528 A | 5/1996 | Tom et al. |
| 5,570,743 A | 11/1996 | Padgett et al. |
| 5,641,245 A | 6/1997 | Pemberton et al. |
| 5,707,500 A | 1/1998 | Shimamura et al. |
| 5,815,396 A | 9/1998 | Shimamura et al. |
| 5,826,607 A | 10/1998 | Knutson et al. |
| 5,887,611 A | 3/1999 | Lampotang et al. |
| 6,050,283 A * | 4/2000 | Hoffman et al. ............ 137/3 |
| 6,067,840 A | 5/2000 | Chelvayohan et al. |
| 6,070,600 A | 6/2000 | Grootegoed et al. |
| 6,089,027 A * | 7/2000 | Wang et al. ............ 62/46.1 |
| 6,171,641 B1 | 1/2001 | Okamoto et al. |
| 6,190,436 B1 | 2/2001 | Ji et al. |
| 6,406,555 B1 | 6/2002 | Grootegoed et al. |
| 6,453,924 B1 | 9/2002 | Wang et al. |
| 6,612,317 B2 | 9/2003 | Costantini et al. |
| 6,617,175 B1 | 9/2003 | Arno |
| 6,631,334 B2 | 10/2003 | Grosshart |
| 6,689,252 B1 | 2/2004 | Shamouilian et al. |
| 6,772,781 B2 | 8/2004 | Doty et al. |
| 6,780,319 B1 | 8/2004 | Thieblin et al. |
| 6,810,821 B2 | 11/2004 | Chan |
| 6,909,973 B2 | 6/2005 | Arno |
| 6,953,731 B2 | 10/2005 | Shinriki et al. |
| 7,058,519 B2 | 6/2006 | Arno |
| 7,063,097 B2 | 6/2006 | Arno et al. |
| 7,122,797 B2 | 10/2006 | Guo et al. |
| 2001/0032668 A1 * | 10/2001 | Doty et al. ............ 137/93 |
| 2002/0048213 A1 * | 4/2002 | Wilmer et al. ............ 366/136 |
| 2004/0007180 A1 | 1/2004 | Yamasaki et al. |
| 2004/0050326 A1 | 3/2004 | Thllderkvist et al. |
| 2005/0006799 A1 | 1/2005 | Gregg et al. |
| 2006/0217896 A1 | 9/2006 | Arno |

* cited by examiner

IN-SITU GAS BLENDING AND DILUTION SYSTEM FOR DELIVERY OF DILUTE GAS AT A PREDETERMINED CONCENTRATION

CROSS-REFERENCE TO RELATED APPLICATIONS

This is a continuation of U.S. patent application Ser. No. 10/402,759 filed Mar. 28, 2003 now U.S. Pat. No. 7,063,097 in the names of Jose I. Arno, et al. for "In-Situ Gas Blending and Dilution System for Delivery of Dilute Gas at a Predetermined Concentration," the entirety of which is incorporated herein by reference for all purposes. Priority of said U.S. patent application Ser. No. 10/402,759 is claimed under the provisions of 35 USC 120.

FIELD OF THE INVENTION

The present invention relates to apparatus and method for supplying dilute gases at predetermined concentrations, e.g., as source gas for ion implantation doping of semiconductor materials.

DESCRIPTION OF THE RELATED ART

The semiconductor industry uses a wide variety of dilute gases in applications where the source material is highly toxic or hazardous and the dosage of active gas species is small.

For instance, chemical vapor deposition doping of epitaxial films requires source gases such as arsine, phosphine, and germane in highly dilute states. As an example, arsenic may be introduced in a semiconductor film for doping thereof, from a dilute arsine/hydrogen gas mixture. In such arsenic doping application, a source gas of low arsine content e.g., 50 parts per million (ppm) may be further diluted with hydrogen to achieve a desired hydrogen/arsine gas mixture. The flows of the dilute arsine starting material and the diluent hydrogen that is added thereto to form the final dilute arsine gas mixture can be controlled by mass flow controllers, to deliver a metered amount of the final diluted arsine to the vapor deposition tool.

Generally, two primary approaches are utilized in the semiconductor industry for supplying an active gas (such term being used hereinafter to designate the gas component of interest, such as the dopant gas species) in diluted form in a gas mixture useful for a desired application.

A first category of dilute gas supply techniques utilizes pre-mixed high-pressure gas mixtures (containing the low-concentration active gas component) as the source gas medium, as dispensed for use from high-pressure gas supply vessels such as pressurized gas cylinders. This gas supply approach has the following deficiencies:

(1) the gas supply vessels are exhausted at a high rate, requiring numerous change-outs of the gas supply vessels during the operation of the active gas-consuming process;

(2) when gas supply vessels are changed out as they are exhausted, the active gas-consuming process may need to be re-qualified, since the concentration of active gas supplied from a freshly installed gas supply vessel may be different from the concentration dispensed from a previously installed gas supply vessel;

(3) in addition to deficiency (2), the gas concentration of the active gas dispensed from any given gas supply vessel is fixed by the gas supply vessel manufacturer, and there is no capability of delivering varying concentrations depending on time-varying conditions in the downstream active gas-consuming process;

(4) the concentration of the active gas in the gas mixture stored in the gas supply vessel can change with time due to decomposition of the active gas component, or the concentration of the active gas can vary with successive change-outs of gas supply vessels, in an unknown and unexpected manner; and (5) the gas supply vessel typically is at high atmospheric pressure to maximize inventory of the active gas in the vessel, entailing a potentially unsafe situation if the gas supply vessel ruptures or leakage from the associated head assembly, valves, etc. of the vessel occurs.

The second general category of dilute gas supply techniques involves in-situ generation of gas, using solids or liquid raw materials to generate the desired gas species through chemical reaction. In-situ gas generation has the following associated deficiencies:

(1) the time required to initiate gas generation and achieve steady-state gas production is generally substantial and does not permit a quick-response turn-on of gas dispensing to be achieved;

(2) the raw materials used as reactants for in-situ gas generation are frequently highly toxic in character, thereby raising safety and operational issues;

(3) in-situ gas generators are typically relatively complex systems, including for example, gas generation chambers, reactant supplies, reactant flow circuitry (since even in the case of solid reactant sources, there is typically a fluid co-reactant), dispensing lines, and associated in-line filters, purifiers, interlocks, etc.;

(4) in-situ gas generators as conventionally employed involve consumable parts requiring periodic replacement, e.g., filters and purifiers; and (5) in-situ gas generation systems are relatively expensive, both in capital expenditure and in overall cost of ownership.

Accordingly, the semiconductor industry has continuing need for improved gas supply sources for delivery of dilute gases to process equipment.

SUMMARY OF THE INVENTION

The present invention relates to apparatus and method for delivery of dilute active gas, e.g., to a downstream active gas-consuming process unit of a semiconductor manufacturing plant.

In one aspect, the present invention relates to an system for delivery of dilute gases, comprising:

an active gas source;

a diluent gas source;

a gas flow metering device for dispensing of the active gas at a predetermined flow rate;

a mixing device arranged to mix active gas from the neat active gas source that is dispensed at said predetermined flow rate by the gas flow metering device, with diluent gas to form a diluted active gas mixture; and a monitor arranged to measure concentration of active gas in the diluted active gas mixture, and responsively adjust the gas flow metering device, to control the dispensing rate of the active gas, and maintain a predetermined concentration of active gas in the diluted active gas mixture.

In another aspect, the invention relates to a system for delivery of dilute fluid, comprising:

an active fluid source;

a diluent fluid source;

a fluid flow metering device for dispensing of the neat active gas at a predetermined flow rate;

a mixing device arranged to mix active fluid from the active fluid source that is dispensed at said predetermined flow rate by the fluid flow metering device, with diluent fluid to form a diluted active fluid mixture; and a monitor arranged to measure concentration of active fluid in the diluted active fluid mixture, and responsively adjust the fluid flow metering device, to control the dispensing rate of the active fluid, and maintain a predetermined concentration of active fluid in the diluted active fluid mixture.

Yet another aspect of the invention relates to a method for delivery of dilute gas, comprising:

providing an active gas source and a diluent gas source;

controllably dispensing active gas from the active gas source at a predetermined flow rate;

mixing active gas from the active gas source that is dispensed at said predetermined flow rate, with diluent gas from the diluent gas source, to form a diluted active gas mixture; and monitoring concentration of active gas in the diluted active gas mixture, and responsively adjusting the dispensing rate of the neat active gas, to maintain a predetermined concentration of active gas in the diluted active gas mixture.

A still further aspect of the invention relates to a method for delivery of dilute fluid, comprising:

providing an active fluid source and a diluent fluid source;

controllably dispensing active fluid from the active fluid source at a predetermined flow rate;

mixing active fluid from the active fluid source that is dispensed at said predetermined flow rate, with diluent fluid from the diluent fluid source, to form a diluted active fluid mixture; and monitoring concentration of active fluid in the diluted active fluid mixture, and responsively adjusting the dispensing rate of the active fluid, to maintain a predetermined concentration of active fluid in the diluted active fluid mixture.

Other aspects, features and embodiments will be more fully apparent from the ensuing disclosure and appended claims.

DETAILED DESCRIPTION OF THE INVENTION AND PREFERRED EMBODIMENTS THEREOF

Figure 1:
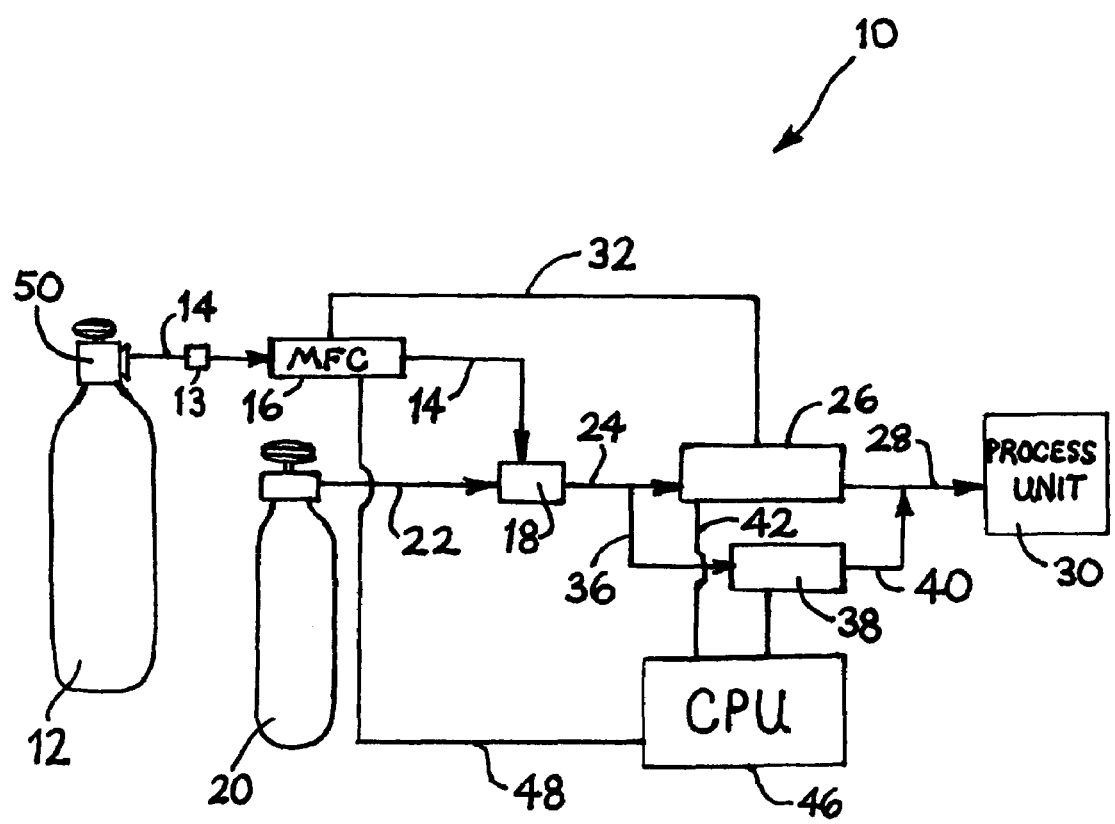
FIG. 1 is a schematic representation of a dilute gas supply system according to one embodiment of the present invention.

The disclosures of copending U.S. patent application Ser. No. 10/402,759 filed Mar. 28, 2003 is hereby incorporated herein by reference in its respective entirety, for all purposes.

The present invention is based on the discovery of a highly efficient and cost-effective system for delivery of dilute gases, utilizing a neat active gas source, a diluent gas source, a gas flow metering device for dispensing of the neat active gas, a dynamic mixing device arranged to mix the neat active gas and the diluent gas for forming a diluted active gas mixture, and a monitor arranged to measure concentration of active gas in the diluted active gas mixture, and responsively control the dispensing rate of the neat active gas, to achieve a predetermined concentration of active gas in the diluted active gas mixture.

In a specific embodiment, as hereinafter described in greater detail, the gas flow metering device comprises a mass flow controller in a gas flow line interconnecting the neat active gas source and the dynamic mixing device, and the monitor comprises an in-line gas analyzer arranged to produce an output control signal correlative to the sensed active gas concentration in the diluted active gas mixture, with the control signal being transmitted to the mass flow controller to modulate the set point thereof to achieve a predetermined constant active gas concentration for the desired application of the diluted active gas mixture.

The gas flow metering device can be of any suitable type, including for example a mass flow controller, a micro-valve element actuatable for dispensing very low flow rates of the active gas component from the active gas supply, a flowmeter coupled with a flow control valve in the dispensing line, or any other element or assembly that is effective to provide a selected flow rate of the active gas from the active gas source.

The active gas source can likewise be of any suitable type, e.g., a high-pressure or low-pressure gas storage and dispensing vessel or container holding the neat active gas to be diluted for use. In one embodiment, the neat active gas source comprises a sub-atmospheric pressure neat active gas storage and dispensing vessel of the type described in U.S. Pat. No. 5,518,528 to Glenn M. Tom et al. and commercially available from ATMI, Inc. (Danbury, Conn.) under the trademark SDS, wherein active gas is sorptively retained on a physical adsorbent and selectively desorbed therefrom for dispensing of active gas from the vessel. In another embodiment, the neat active gas source comprises a gas storage and dispensing vessel of the type described in U.S. Pat. No. 6,089,027 to Luping Wang, et al. and commercially available from ATMI, Inc. (Danbury, Conn.) under the trademark VAC, featuring an interiorly disposed regulator element for dispensing of the active gas at a pressure determined by the regulator set point.

The dynamic mixing device arranged to mix the neat active gas and the diluent gas for forming a diluted active gas mixture can be of any suitable type, whereby the neat active gas and the diluent gas are intermixed with one another for discharge at a desired dilute concentration of the active gas, e.g., for flow to the downstream dilute gas mixture-consuming process. The dynamic mixing device can for example comprise a venturi, static mixer, pump, compressor, rotary mixer, ejector, eductor, opposed jet-equipped mixing chamber, or other device, structure or assembly that effects mixing of the neat active gas and the diluent gas to produce the diluted active gas mixture.

The monitor arranged to measure concentration of active gas in the diluted active gas mixture, and responsively control the dispensing rate of the neat active gas, to achieve a predetermined concentration of active gas in the diluted active gas mixture, can be of any suitable type, including spectrometric, chromatographic, calorimetric, surface acoustic wave (SAW), photonic and flame ionizer types. Preferred monitor types include Fourier Transform-Infrared (FT-IR) and IR photometric monitors. The monitor can be arranged in any suitable manner, e.g., disposed in-line in the diluted active gas mixture discharge line, or disposed to sample gas via a side-stream sampling arrangement, or in any other suitable fashion.

The monitor can include one or multiple monitoring devices or components, as desired in a given application of the invention. In instances where multiple monitor devices are employed, to provide monitoring via different sensing modalities, the signals generated by each of the constituent monitoring devices or components that are indicative of the concentration of the active gas in the diluted active gas mixture can be processed to provide an average or corrected output signal correlative to the concentration of the active gas in the diluted active gas mixture.

Such signal processing can be carried out by a programmable general purpose computer that is programmed to process the respective output signals of the respective monitoring devices or components according to a suitable algorithm or computational procedure to provide a net output signal correlative of the concentration of the active gas in the diluted active gas mixture. Alternatively, the signal processing can be carried out by a comparator or bridge circuit, microprocessor, central processing unit (CPU) or other processor, to provide appropriate output for modulating the gas flow metering device to achieve the desired active gas concentration in the diluted active gas mixture.

In a preferred embodiment, the monitor type includes an infrared thermopile detector system such as the type discussed in U.S. patent application Ser. No. 10/140,484, having a United States filing date of May 8, 2002, which is hereby incorporated herein by reference in its entirety. In such a system a radiation source transmits infrared radiation through a sample of the gas stream, and a thermopile detector receives the infrared radiation after transmission through the gas sample. A signal correlative of concentration of at least one component in the gas sample, which is preferably the active gas component, is output to a control means arranged to receive the output of the thermopile detector and to responsively control one or more process conditions in and/or affecting the system.

The active gas in the dilute gas supply system of the invention can be of any suitable type, depending on the specific diluted active gas mixture-using process for which the diluted active gas mixture is to be provided. The gas can for example be a gas that is a source material for forming a dopant or trace reagent species, for manufacturing of semiconductor products. The gas alternatively could be diluted for use as a calibration standard, as a sterilant for use below hazardous concentration levels, as a reactant for nano-concentration chemical reactions, for preparation of low concentration mutagenic agent samples, for research and testing purposes, etc.

The diluted active gas mixture-using process can be correspondingly varied, and can variously include industrial processes (e.g., chemical vapor deposition), medical diagnostics, research investigations, agricultural assays, treatment of the body with dilute radiological therapeutic agents, etc.

The diluent gas can be of any suitable type, and can variously include single component diluent compositions, as well as multi-component diluent formulations. Illustrative of potentially suitable diluent gases in specific applications of the invention are nitrogen, argon, helium, air, krypton, xenon, xenon halides, hydrogen, oxygen, ammonia, and gaseous organometallic compounds, etc.

Referring now to the drawings, FIG. 1 is a schematic representation of a dilute gas supply system 10 including a neat active gas source 12, which may for example compromise a fluid storage and dispensing vessel such as a conventional high-pressure gas cylinder or alternatively a sub-atmospheric pressure gas dispensing system, e.g., of the type disclosed in U.S. Pat. No. 5,518,528 to Glenn M. Tom, et al and U.S. Pat. No. 6,089,027 to Luping Wang, et al, the disclosures of which hereby are incorporated herein by reference in their respective entireties.

The neat active gas source 12 thus may comprise a vessel equipped with a valve head 50, as shown, or alternatively coupled with an external regulator, restricted orifice flow control element(s) 13, and other conventional flow circuitry elements. The valve head 50 can contain a conventional flow control valve (head valve) controllable by a hand wheel actuator, as illustrated, or alternatively by an automatic valve controller, e.g., a pneumatic actuator, or electrical solenoid valve actuator, etc.

The neat active gas source 12 is coupled in closed gas flow communication with discharge line 14 having mass flow controller 16 disposed therein. The discharge line 14 downstream of the mass flow controller 16 is coupled to venturi 18, with the venturi providing suction for inducing flow of neat active gas from discharge line 14 into the throat of the venturi.

A dilute gas source 20 is provided in the system, and arranged to discharge diluting gas in line 22, which may optionally include a mass flow controller, to venturi 18 for flow therethrough and discharge from the venturi in line 24 containing in-line gas analyzer 26 therein.

The in-line gas analyzer 26 is constructed and arranged to generate an output control signal indicative of the concentration of the active gas in the diluted gas stream flowing through the analyzer from fine 24 and dispensed from the analyzer 26 in line 28 for flow to downstream gas-using process unit 30, e.g., an epitaxial growth facility or other semiconductor process tool or installation.

The electronic signal generated by in-line analyzer 26 is transmitted in signal transmission line 32 to mass flow controller 16, which responsively adjusts flow rate of the neat active gas in discharge line 14 that is flowed to the venturi 18 for dilution to produce the product gas for downstream use.

In operation, neat (100% concentration) active gas is dispensed from neat gas source 12 into discharge line 14 containing mass flow controller 16, which operates to control the delivery rate of the neat gas. The resulting modulated flow rate neat gas in discharge line 14 is mixed with the diluting gas stream flowed from diluting gas source 20 through line 22 to venturi 18. In lieu of a venturi device, a device such as an eductor or pump, with or without a static mizer, can alternatively be employed to mix the diluting gas with the active gas. The venturi or other mixing device provides necessary pressure differential across the mass flow controller 16 to flow the active gas through the flow circuit of the overall supply system. The resulting mixed dilute gas stream (including the active gas and diluting gas) is flowed in line 24 to the in-line gas analyzer 26, where concentration of active gas in the gas mixture is determined and used to responsively generate the control signal transmitted in signal transmission line 32 to the mass transfer controller, with the mass flow controller responsively being modulated by the control signal to increase or decrease the active gas delivery rate to achieve the desired diluted active gas concentration in the diluted active gas mixture in line 28 flowed to the downstream process unit 30.

The in-line gas monitor/analyzer 26 can operate by any suitable mode of operation, including for example, photometry, spectroscopy, electrochemistry, acoustic monitoring, thermal monitoring, etc., or a combination of two or more of such modes of operation, to determine concentration of active gas in the gas mixture as diluted for flow to the downstream gas-using process.

In a variation of the process just described, in which the dilute gas mixture monitor comprises in-line monitor 26, the process system can alternatively or additionally utilize a bypass or side-stream loop including take-off line 36 interconnecting line 24 with monitor 38 and recycle line 40 joining monitor 38 with line 28. The monitor 38 generates an output control signal correlative of the concentration of the active gas in the bypass loop and such output control signal is transmitted by signal transmission line 44 to the central processing unit (CPU) 46. The central processing unit 46 in turn processes the concentration signal from line 44 and transmits a correspondingly processed signal in signal transmission line 48 to the mass flow controller 16.

As a still further variation of the system described above, the CPU 46 can also be arranged to concurrently receive concentration output signal in line 42 from the in-line monitor 26, whereby the signals from both concentration-monitoring monitors 26 and 38 are processed in CPU 46 and used to generate a unitary control signal that is transmitted in signal transmission line 48 to the mass flow controller 16. By such arrangement, the system is arranged to process two concentration-sensing signals from the corresponding monitors 26 and 38, e.g., with the respective monitors operating by a same or different monitoring modality in relation to one another, to enhance the accuracy and reliability of the control signal sent to the mass flow controller 16.

The active gas as mentioned can be of any suitable type, including for example, in the case of semiconductor process usage, gases such as hydrides (e.g., arsine, phosphine, germane, etc.), acid gases (e.g., $SiHCl_3$, $SiF_4$, $SiH_2Cl_2$), boranes, etc. Diluting gases for such semiconductor manufacturing applications can include, for example, homonuclear diatomic species (e.g., $H_2$, $N_2$, $O_2$) or atomic gases (e.g., argon, helium, and the like).

It will be recognized that while the invention is illustratively shown with reference to delivery of dilute gas species, the invention is also amenable to delivery of blends of materials in the liquid phase including an active liquid of a desired concentration.

It will also be recognized that the dilute fluid supply system of the invention can be operated and arranged to supply a plurality of active species, e.g., a blend of complex dopants.

The safety advantages of utilizing the system of the present invention are enhanced when the active gas source is a sub-atmospheric gas source such as those of the aforementioned Tom, et al and Wang, et al patents.

Thus, the present invention, by virtue of utilizing a real-time gas monitor provides a continuous measure of the gas mixture, thereby ensuring a constant diluted active gas concentration in the delivered dilute gas mixture, in contrast to the conventional methods described earlier herein in the Background of the Invention section hereof. If active gas concentration deviates from a set point value, a control signal is sent from the gas monitor to the active gas metering device to increase or decrease the active gas delivery rate to maintain the desired concentration value.

The features and advantages of the invention are more fully shown by the following non-limiting example.

EXAMPLE 1

Utilizing a system of the type shown in FIG. 1, the operation of the invention was demonstrated with carbon tetrafluoride ($CF_4$) as the active gas. The active gas source was a sub-atmospheric pressure VAC® gas source vessel (commercially available from ATMI, Inc., Danbury, Conn.) equipped with an internal gas regulator for constant delivery pressure of carbon tetrafluoride at 500 torr.

The gas was dosed using a micro-valve connected to the gas source vessel and capable of delivering a sub-milliliter per minute flow rate, to produce the low concentration mixtures desired. The fluid dispensing operation was controlled by adjusting the rate of valve opening and closing a valve using a fast-speed solenoid.

In order for the micro-valve to deliver gas, a pressure differential between the inlet and outlet of the valve was required. This pressure differential was provided by a small venturi pump driven with a 60-psi supply of nitrogen gas, with the nitrogen gas being the diluent gas for the diluted product gas mixture. The turbulence created in the high-to-low pressure interface of the venturi pump provided the necessary mixing of the neat gas and the diluent gas.

Figure 2:
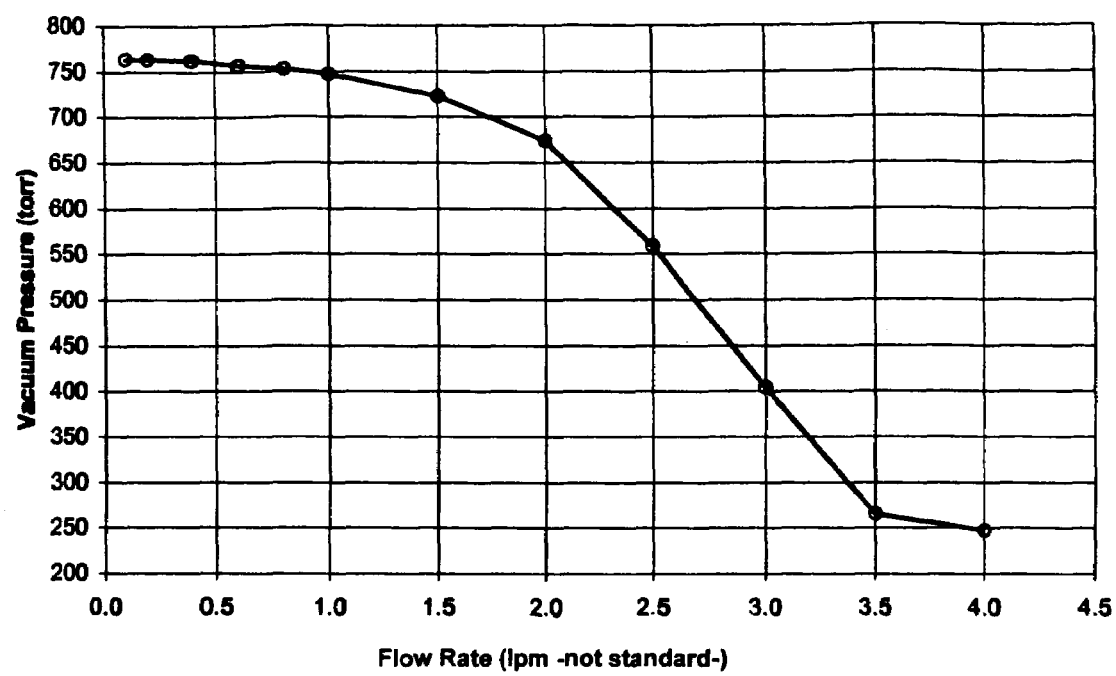
FIG. 2 is a graph of vacuum pressure, in torr as a function of flow rate in liters per minute, illustrating the vacuum levels achieved using a mini-venturi in the practice of the present invention.

FIG. 2 illustrates the vacuum pressure levels that were achieved using the venturi pump, with the vacuum pressure being shown as a function of diluent nitrogen flow rate. As an illustrative example, a flow of nitrogen gas at 4 standard liters per minute (slpm) at 60 psi (equivalent to 7.8 slpm at 14.7 psi) produced a vacuum of 250 torr. The pressure differential between the inlet of the micro-valve (at 500 torr) and the outlet of the micro-valve (at 250 torr) was adequate to produce the desired gas flow.

The resulting carbon tetrafluoride/nitrogen gas mixture was introduced to two in-line gas analyzers. The first analyzer was a commercially available Fourier Transform-Infrared (FT-IR) spectrometer. The second gas analyzer was an infrared photometer including a broad band infrared (IR) light source and a dual channel filtered thermopile detector.

In the photometer, one filter element was employed to block all IR energy except for the region where the active species (carbon tetrafluoride) absorbed light. The second filter element in the photometer filtered out all IR energy with the exception of a narrow band at a region where no common materials absorbed light, thereby enabling the second filter element to be employed for reference signal purposes. This photometer system is of a simple character, involving no moving parts, and provided an analog signal proportional to the concentration of the active gas ($CF_4$).

Figure 3:
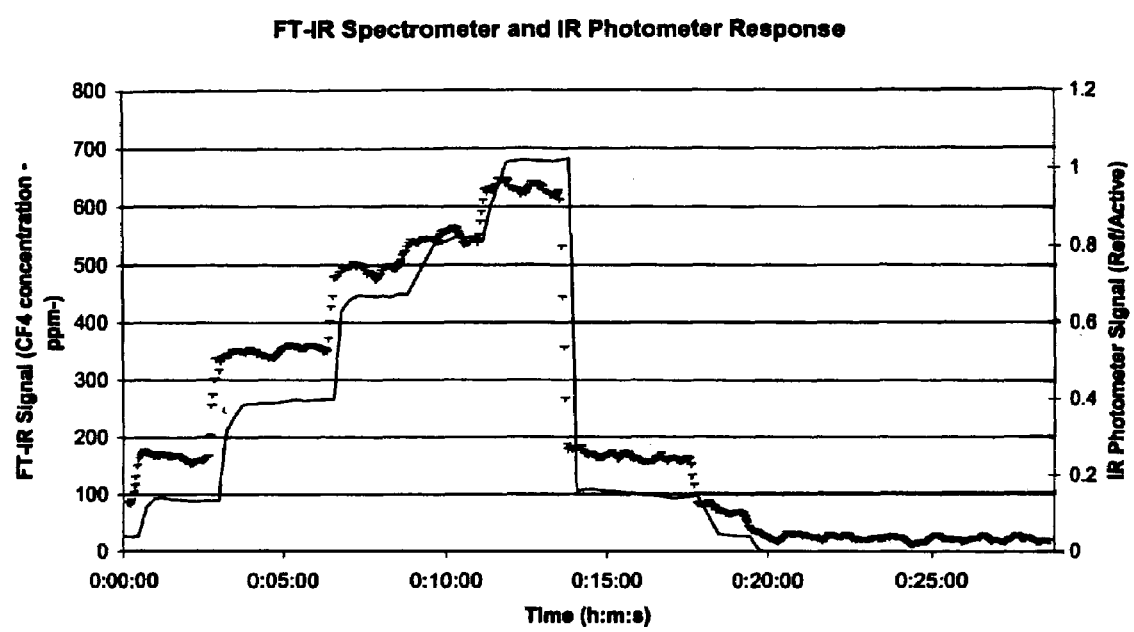
FIG. 3 is a graph showing FT-IR signal of carbon tetrafluoride concentration in parts per million as a function of time, in hours: minutes: seconds, and corresponding IR photometer signal (reference/active) as a function of time.

FIG. 3 shows the time-dependent signals from the IR photometer and FT-IR analyzer with changing $CF_4$ delivery rates. While the FT-IR signal was of a delayed nature due to computational duration associated with the FT-IR device, the IR photometer provided accurate and fast response to changing conditions.

FIG. 3 also illustrates the utility of the micro-valve for controlling the delivery rate of small flows of the active gas. For example, a concentration of 100 parts per million by volume (ppmv) of $CF_4$ per standard liter per minute (slpm) of $N_2$ corresponded to delivery of 0.7 standard cubic centimeters per minute (sccm) of $CF_4$. Smaller flow rates are achievable by reducing the pressure inside the valve, or by introducing a flow restriction between the outlet of the valve and the inlet of the venturi.

Figure 4:
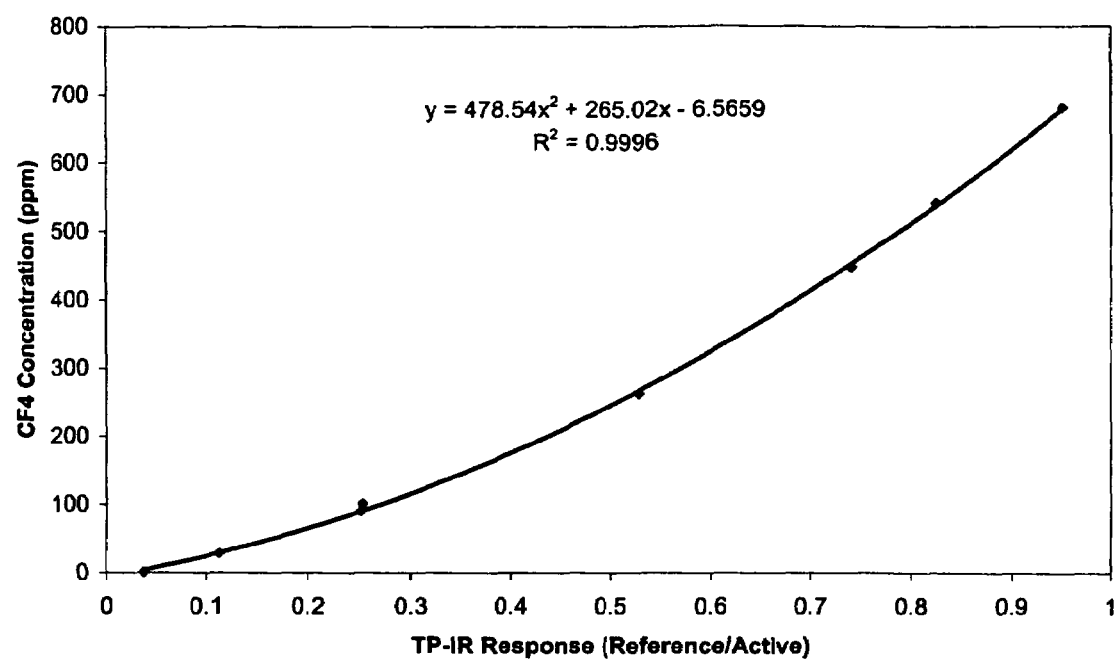
FIG. 4. is a calibration curve plotted as carbon tetrafluoride concentration, in parts per million, as a function of FT-IR response (reference/active) and showing the corresponding calibration algorithm.

FIG. 4 shows a calibration curve of the IR photometer, generated by comparing the FT-IR calibrated signal to the reference signal from the IR photometer.

The foregoing example illustrates the utility of the invention in delivering small flow rates of an active gas, as mixed, measured and dynamically controlled using a simple feedback loop between an analyzer and a gas flow metering component.

While the invention has been described herein with reference to specific aspects, features and embodiments, it will be recognized that the invention is not thus limited, but is susceptible to implementation in numerous other variations, modifications, and alternative embodiments.

Accordingly, the invention is intended to be broadly construed as encompassing such variations, modifications and alternative embodiments, within the spirit and scope of the invention as hereinafter claimed.

What is claimed is:

1. A material blender system adapted for coupling with an active material source providing an active material flow and for coupling with a diluent material source providing a diluent material flow, and adapted to deliver a controllable flow of a diluted active material mixture to an active-material-consuming process facility, the material blender system comprising:
    a material flow metering device for dispensing the active material;
    a mixing device arranged to mix the active material flow with the diluent material flow to form a diluted active material mixture;
    a monitor arranged to measure concentration of active material in the diluted active material mixture; and
    a control element arranged to receive a signal correlative of active material concentration from the monitor and to responsively adjust the material flow metering device to control the dispensing rate of the active material, and maintain a predetermined concentration of active material in the diluted active material mixture;
    wherein at least one of the active material flow and the diluent material flow is provided to the mixing device without passage through a mass flow controller and without passage through a flow restriction element.

2. The material blender system of claim 1, wherein the control element comprises a central processing unit.

3. The material blender system of claim 1, wherein the control element is integrated with the monitor.

4. The material blender system of claim 1, wherein the material flow metering device comprises a mass flow controller.

5. The material blender system of claim 1, further comprising a material flow line communicatively coupled between the active material source and the mixing device, wherein the mass flow controller is disposed in the material flow line.

6. The material blender system of claim 1, wherein the monitor comprises an in-line material analyzer.

7. The material blender system of claim 1, further comprising a bypass material flow loop, wherein the one monitor comprises a first monitor disposed in the bypass material flow loop.

8. The material blender system of claim 1, wherein the material flow metering device comprises a micro-valve.

9. The material blender system of claim 1, wherein the mixing device comprises a venturi, and the material flow metering device comprises a valve and a restricted flow orifice between the valve and the venturi.

10. The material blender system of claim 1, wherein the active material source comprises a material storage and dispensing vessel holding the active material.

11. The material blender system of claim 10, wherein the material storage and dispensing vessel contains a sorbent medium sorptively retaining active material material, and from which active material is desorbed for dispensing of active material from the vessel.

12. The material blender system of claim 11, wherein said sorbent medium is a solid.

13. The material blender system of claim 10, wherein the material storage and dispensing vessel contains an interiorly disposed regulator for dispensing active material from the vessel at a pressure determined by a set point of the regulator.

14. The material blender system of claim 1, wherein the mixing device comprises any of a venturi, a static mixer, a pump, a compressor, a rotary mixer, an ejector, an eductors, and an opposed-jet-equipped mixing chamber.

15. The material blender system of claim 1, wherein the mixing device comprises a venturi.

16. The material blender system of claim 1, wherein the monitor comprises a material monitoring device including any of a spectrometric, chromatographic, colorimetric, surface acoustic wave (SAW), photonic, and flame ionizer monitor.

17. The material blender system of claim 1, wherein the monitor comprises a Fourier Transform-Infrared (FT-IR) analyzer.

18. The material blender system of claim 1, wherein the monitor comprises an IR photometer.

19. The material blender system of claim 1, wherein the monitor comprises a Fourier Transform-Infrared (FT-IR) analyzer and an IR photometer.

20. The material blender system of claim 1, wherein the monitor comprises multiple material monitoring devices.

21. The material blender system of claim 20, wherein said multiple monitoring devices comprise material monitoring devices having differing material concentration sensing modalities.

22. The material blender system of claim 1, wherein the active-material-consuming process facility comprises a semiconductor manufacturing plant.

23. The material blender system of claim 22, wherein the semiconductor manufacturing plant comprises any of an ion implantation unit and a chemical vapor deposition process unit.

24. The material blender system of claim 1, wherein the diluent material comprises any of nitrogen, argon, helium, air, krypton, xenon, xenon halides, hydrogen, oxygen, ammonia, and gaseous organometallic compounds.

25. The material blender system of claim 1, wherein the active material comprises any of arsine, phosphine, germane, $SiHCl_3$, $SiF_4$, and $SiH_2Cl_2$.

26. The material blender system of claim 1, wherein the active material comprises a hydride selected from the group consisting of arsine, phosphine, and germane.

27. The material blender system of claim 1, wherein the monitor is adapted to continuously measure concentration of active material in the diluted active material mixture.

28. The material blender system of claim 1, further comprising a discharge conduit disposed downstream of the monitor and adapted for fluid communication with the material-consuming process facility, wherein the material blender system is adapted to deliver the diluted active gas mixture comprising all of the active material flow to the discharge conduit.

29. The material blender system of claim 1, wherein each of the active material and the diluent material comprises a fluid.

30. The material blender system of claim 1, wherein each of the active material and the diluent material comprises a gas.

31. The material blender system of claim 1, wherein each of the active material and the diluent material comprises a liquid.

32. A material blender system adapted to receive an active material flow from an active material source and to receive a diluent material flow from a diluent material source, and adapted to deliver a controllable flow of a diluted active material mixture to an active-material-consuming process facility, the material blender system comprising:
- a material flow metering device adapted to dispense at least one of the active material and the diluent material;
- a mixing device arranged to mix the active material flow with the diluent material flow to form a diluted active material mixture;
- a monitor arranged to measure concentration of active material in the diluted active material mixture; and
- a central processing unit arranged to receive a signal correlative of active material concentration from the monitor and to responsively adjust the material flow metering device to control the dispensing rate of any of the active material and the diluent material, and maintain a predetermined concentration of active material in the diluted active material mixture;

wherein at least one of the active material flow and the diluent material flow is provided to the mixing device without passage through a mass flow controller and without passage through a flow restriction element.

33. The material blender system of claim 32, wherein the material flow metering device is adapted to dispense the active material.

34. The material blender system of claim 32, wherein the monitor is adapted to continuously measure concentration of active material in the diluted active material mixture.

35. The material blender system of claim 32, wherein the monitor comprises multiple material monitoring devices.

36. The material blender system of claim 35, wherein said multiple monitoring devices comprise material monitoring devices having differing material concentration sensing modalities.

37. The material blender system of claim 32, wherein the active-material-consuming process facility comprises a semiconductor manufacturing plant.

38. The material blender system of claim 32, further comprising a discharge conduit disposed downstream of the monitor and adapted for fluid communication with the material-consuming process facility, wherein the material blender system is adapted to deliver the diluted active material mixture comprising all of the active material flow to the discharge conduit.

39. The material blender system of claim 32, wherein each of the active material and the diluent material comprises a fluid.

40. The material blender system of claim 32, wherein each of the active material and the diluent material comprises a gas.

41. The material blender system of claim 32, wherein each of the active material and the diluent material comprises a liquid.

* * * * *